United States Patent [19]

Nissinen

[11] 4,078,559

[45] Mar. 14, 1978

[54] STRAIGHTENING AND SUPPORTING DEVICE FOR THE SPINAL COLUMN IN THE SURGICAL TREATMENT OF SCOLIOTIC DISEASES

[76] Inventor: Erkki Einari Nissinen, Wredenkatu 3 A 15, 78100 Varkaus 10, Finland

[21] Appl. No.: 690,131

[22] Filed: May 26, 1976

[30] Foreign Application Priority Data

Oct. 6, 1975 Finland .................................. 751604

[51] Int. Cl.² .............................................. A61F 5/01
[52] U.S. Cl. ...,..................................... 128/69; 128/75; 128/78; 128/92 R
[58] Field of Search ................... 128/69, 75, 78, 92 R, 128/92 A, 92 B, 92 E, 84 R, 84 A, 84 B, 84 C, 92 D, 92 BC

[56] References Cited

U.S. PATENT DOCUMENTS 3,693,616  9/1972  Roaf et al. ..................... 128/92 R X

OTHER PUBLICATIONS

Journal of Bone and Joint Surgery, vol. 53a, No. 2, Mar. 1971, p. 57, by A. F. Dwyer, M.B., M.S., F.R.A.C.S.

Primary Examiner—Robert W. Michell
Assistant Examiner—Michael H. Thaler
Attorney, Agent, or Firm—Frank J. Jordan

[57] ABSTRACT

Disclosured is a straightening and supporting device for the spinal column in the surgical treatment of scoliotic diseases, a device which is removed after the spinal column has healed. The device comprises a rod-shaped supporting member at least the length of the spinal column area to be treated and wires bearing on the ends of the supporting member and exerting a straightening and supporting effect on the vertebrae of the spinal column. Additionally, attachment members with loops, some of which being resilient, are arranged to the vertebrae, the wires being capable of sliding in the loops.

6 Claims, 2 Drawing Figures

STRAIGHTENING AND SUPPORTING DEVICE FOR THE SPINAL COLUMN IN THE SURGICAL TREATMENT OF SCOLIOTIC DISEASES

BACKGROUND OF THE INVENTION

The present invention relates to a straightening and supporting device for the spinal column in the surgical treatment of scoliotic diseases; the device is removed when the spinal column has healed and comprises a rod-shaped supporting member at least the length of the spinal column area to be treated and tractive members, connected to the supporting member, which exert a straightening and supporting effect on the vertebrae.

Scoliosis means curvature of the spinal column. Scoliosis is a symptom of a disease of which all the basic causes are not yet known. When it becomes more serious it results in deformation of the thorax, which again can have a deteriorating effect on the function of the heart and the lungs. A very great increase in the curvature can shorten the patient's life span. Scoliosis develops most strongly during adolescence.

The treatment methods used for scoliosis have been supporting girdles outside the body, such as the Milwaukee support, and surgical techniques.

In surgical treatment the Harrington rod has been employed which is attached with hooks to two vertebrae on the side of the spines in such a manner that the vertebrae to be straightened are left between the attachment vertebrae. By means of the rod the attachment vertebrae are brought farther apart from each other, whereby the spinal column is straightened. The rod is left to support the patient's back for even several years.

Also known are surgical methods in which springs are attached to the vertebrae or, as in the Dwyer-Sherwood method, a steel cable is attached by means of screws to the bodies of the vertebrae. A force which presses the vertebrae against each other is produced by tightening the cable. The total effect of the force resisting compression and the tractive tension of the cable constitutes the force which straightens the spinal column.

Furthermore, U.S. Pat. No. 3,565,066 describes a device which has a rod-shaped supporting member provided with threaded openings. Tractive members with hooked ends to be attached to the vertebrae have been screwed into these openings.

The above surgical devices have the disadvantage that the straightening force transmitted by the attaching members is concentrated on only a few vertebrae or that the spinal column itself is substantially used as a transmitter of the straightening force. The force applied cannot surpass the strength of the bone of the vertebrae to which the device is attached or the endurance of the weakest intervertebral space. Scoliosis is also associated with the twisting of the spinal column around itself. Forces which correct the twisting of the vertebrae cannot be controlled in an appropriate manner by means of known surgical straightening devices. The patient's incomplete growth in height also sets limitations or requires changes in the installation of the devices.

SUMMARY OF THE INVENTION

When a device according to the present invention is employed, the spinal column does not substantially serve as a transmitter of the straightening force, and by means of a construction which follows the line of the spinal column the straightening force is distributed evenly between the vertebrae of the area to be straightened. The device according to the invention can be installed to support the straightened area in such a manner that an individual vertebra is subjected to a relatively small load. The device allows the patient's growth in height within predetermined limits without special changes in the installation, and the twisting of the vertebrae around themselves is prevented very effectively by the device. The straightening forces are considerably greater than those obtained at present. (The pressing force of the Harrington rod can be at maximum 25–40 kgf.) Besides, the space requirement of the device is relatively small compared with known devices, e.g., the devices provided with tractive members having hooked ends.

The characteristics of the invention are given in the patent claims below. One or two wires can be employed in a device according to the invention. A device in which only one wire and a rod-shaped supporting member are used and the length of which cannot be regulated is not, however, as safe and sturdy as a device in which two wires are used.

Especially in a device with one wire the twisting of the steel wire around itself can be converted to a force which exerts an effect on the twisting of the vertebrae. In such a case, however, the attaching members of some group of vertebrae must be attached to the wire.

In a device with two wires it is advantageous if the lengths of both the rod-shaped supporting member and one of the wires can be regulated.

The installability and the amount of the forces are affected by the selection of the construction and the materials of the wires and the other parts. The rod-shaped supporting member can be shaped by bending into a form for installation. The construction of the device can be solved in several different ways within the patent claims below. If the rod-shaped supporting member is resilient in its longitudinal direction, it can be installed so that it generates force even after the surgical treatment. At the same time the spinal column retains some resilience against even momentary maximum loads in the lateral direction.

BRIEF DESCRIPTION OF THE DRAWING

One embodiment of the invention is illustrated in the enclosed drawing.

DESCRIPTION OF THE PREFERRED EMBODIMENT

Figure 1:
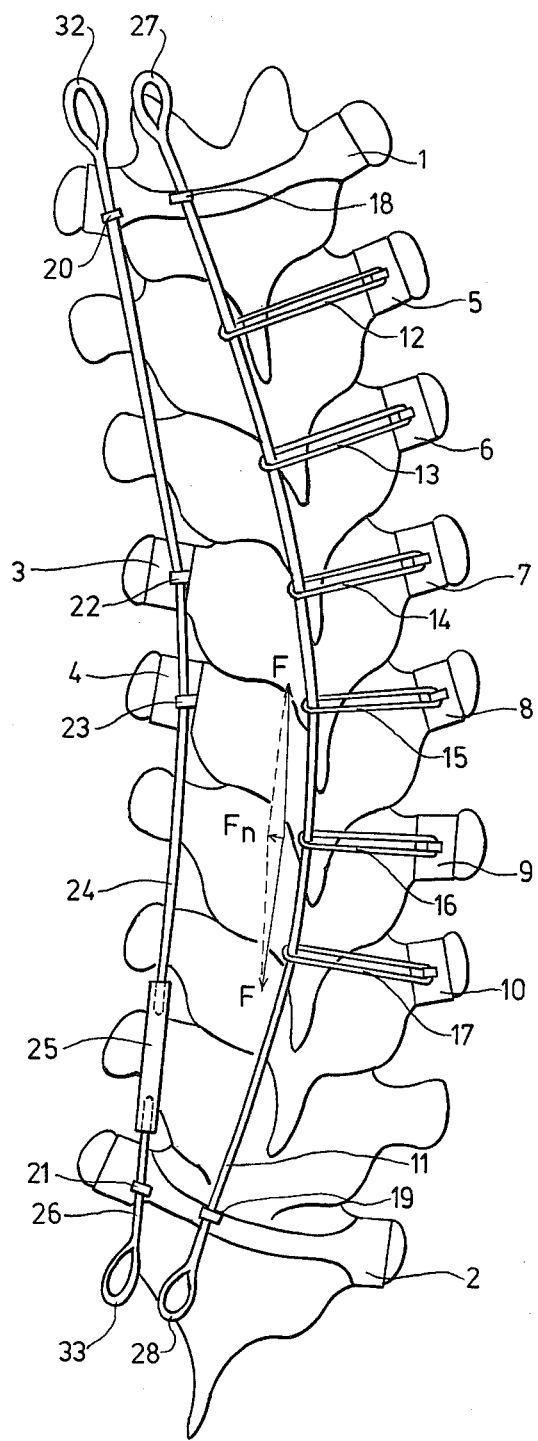
FIG. 1 depicts one way of installing a device according to the invention to vertebrae before they are straightened.

Attachment members 1–10 are attached to the vertebrae by, for example, bending them around the spines of the vertebrae to produce a forceps-like grip. The attachment members 1 and 2 have wire holders 18–21 and the attachment members 3 and 4 have wire holders 22 and 33. The attachment membes 5–10 have loops 12–17 for the wire. The wire 11 is passed through the wire loops 12–17 and the wire holders 18 and 19. The wire 24, 26. is placed in wire holders 20–23. After the straightening the wire 11 is attached by means of the attachment members 27 and 28 at its end to the ends of the rod-shaped supporting member 29, 31 which is adjusted by means of screw 30. A tractive tension for the wire 24, 26 is adjusted by means of a screw 25, whereby the twisting of the vertebrae around themselves is standardized to the desired degree. After straightening and supporting (FIG. 2) the vertebrae are in a straight line but the wire 11 is in a curved line. This situation reduces the tractive tension required in the wire 11, and it is produced by the wire loops 12–17 forming a curved line.

Figure 2:
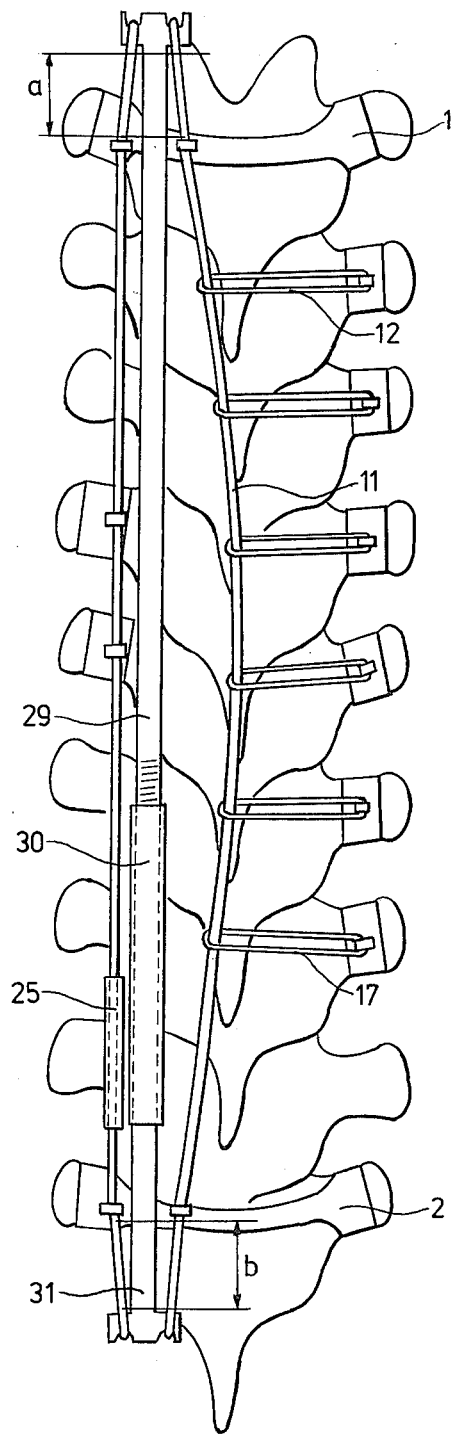
FIG. 2 depicts a device according to the invention after the vertebrae have been straightened and supported.

When a device according to the invention is employed, the straight line along which the active forces exert their effect does not run along the spinal column but along the wires. For this reason the efficiency of the device in maintaining the spinal column straight is not lowered even if the wires 11 and 24, 26 and the rod-shaped supporting member 29, 31 are capable of sliding in relation to the attachment members 1–10 in the direction of the spinal column. In such a case the allowance for the growth of the spinal column is of the order $a+b$ (FIG. 2). Besides, resilience is maintained in the vertebrae under the vertical load of the spinal column.

When the ends of the wire 11 are brought farther apart from each other during surgical treatment, a tractive tension caused by the force F is produced in the wire. The force F exerts its effect in the direction of the wire, evenly over the length of the entire vertebral area to be straightened (FIG. 1). The projection of the force F in the lateral direction of the vertebrae is $F_n$, and it is determined at each vertebra in accordance with the vector principle. The straightening of the spinal column occurs when the sum of the projection forces $$\sum_{n-1}^{n} F_n$$

effective in all vertebrae is greater than the forces resisting the straightening.

The force $F_n$ also produces a moment force which twists the vertebrae around themselves. The moment forces can be directed in different ways during the straightening, e.g., by employing the wire combination 24, 25, 26 by directing the straightening of the spinal column manually.

The wires employed can be, for example, 2–3 mm steel wire or cable. The rod-shaped supporting member can be, for example, a 5–7 mm steel rod. If the length of the effective area of the rod is 20–25 cm, it endures, without buckling, a relatively great load in the direction of its axis.

What is claimed is:

1. A straightening and supporting device for the spinal column in the surgical treatment of scoliotic diseases, said device being removed after the spinal column has healed, said device comprising a rod-shaped supporting member, two resilient tractive wires disposed alongside said supporting member, said tractive wires being mounted on the end portions of said supporting member, a plurality of loops fitted on said wires, at least some of said loops on one of said wires being resilient attachment members adapted to be arranged on the vertebrae of said spinal column, said loops connecting said wires and said attachment members, said wires being capable of sliding in said loops, said wires exerting a straightening and supporting effect to said vertebrae.

2. A device according to claim 1 comprising adjusting means on said rod-shaped supporting member operable to adjust the longitudinal length of said rod-shaped supporting member to thereby regulate the tractive tension of said wires.

3. A device according to claim 1 comprising adjusting means on one of said tractive wires to adjust the longitudinal length of said one tractive wire to thereby regulate the tractive tension of said one tractive wire.

4. A device according to claim 1, wherein the ends of said wires are provided with attachment links with which said ends of said wires are attached to said rod-shaped supporting member after the straightening of the spinal column.

5. A device according to claim 1, wherein said rod-shaped supporting member is resilient in its longitudinal direction in order to produce a potential tractive tension in said wires.

6. A device according to claim 1, wherein said two tractive wires are disposed on opposite sides of said support member.

* * * * *